(12) United States Patent
Erickson et al.

(10) Patent No.: US 8,529,521 B2
(45) Date of Patent: Sep. 10, 2013

(54) LOW-DOSAGE SYRINGE

(75) Inventors: Thomas E. Erickson, Crosslake, MN (US); James J. Erickson, Mound, MN (US)

(73) Assignee: Ultimed Inc., St. Paul, MN (US)

( * ) Notice: Subject to any disclaimer, the term of this patent is extended or adjusted under 35 U.S.C. 154(b) by 337 days.

(21) Appl. No.: 12/107,442

(22) Filed: Apr. 22, 2008

(65) Prior Publication Data

US 2008/0262435 A1 Oct. 23, 2008

Related U.S. Application Data

(60) Provisional application No. 60/913,376, filed on Apr. 23, 2007.

(51) Int. Cl.
*A61M 5/315* (2006.01)

(52) U.S. Cl.
USPC .......................................... 604/218

(58) Field of Classification Search
USPC .................. 604/207, 211, 187, 218
See application file for complete search history.

(56) References Cited

U.S. PATENT DOCUMENTS

| | | |
|---|---|---|
| 827,693 A | 7/1906 | Korb |
| 2,933,087 A | 4/1960 | Hamilton |
| 3,153,496 A | 10/1964 | Johnson |
| 3,216,616 A * | 11/1965 | Blankenship, Jr. ............. 222/47 |
| 3,921,864 A * | 11/1975 | Dawes .......................... 222/386 |
| 3,923,207 A * | 12/1975 | Kyogoku ....................... 222/386 |
| 4,384,581 A | 5/1983 | Conway |
| 5,616,123 A * | 4/1997 | Cheikh ........................... 604/60 |
| 6,004,300 A | 12/1999 | Butcher et al. |
| 6,283,941 B1 | 9/2001 | Schoenfeld et al. |
| 6,585,690 B1 | 7/2003 | Hoeck et al. |
| 2007/0156102 A1 | 7/2007 | Py |
| 2007/0270743 A1 | 11/2007 | Ackerman |

* cited by examiner

*Primary Examiner* — Kevin C Sirmons
*Assistant Examiner* — Brandy S Lee
(74) *Attorney, Agent, or Firm* — Seager, Tufte & Wickhem LLC

(57) ABSTRACT

Low-dosage syringes for use in administering small dosages of medicine are disclosed. An illustrative low-dosage syringe can include an elongate syringe barrel having an interior chamber adapted to receive a supply of fluid, a plunger member slidably disposed within the interior chamber, and a tip member defining an inner lumen in fluid communication with the interior chamber. The configuration of the syringe barrel, including the wall thickness of the barrel relative to the outer diameter and to the length of the barrel, may permit small dosages of medicine to be accurately administered while also allowing the user to easily manipulate the syringe barrel with their fingers.

28 Claims, 5 Drawing Sheets

LOW-DOSAGE SYRINGE

RELATED APPLICATIONS

This application claims priority to U.S. Provisional Application Ser. No. 60/913,376, filed Apr. 23, 2007.

FIELD

The present invention relates generally to the field of medical devices. More specifically, the present invention pertains to low-dosage syringes for use in accurately delivering small dosages of fluids.

BACKGROUND

Medical syringes are available in a large variety of sizes and configurations for delivering liquids or gases to a patient. Syringes are usually equipped with either a nozzle tip or a hypodermic needle for administering medications. Many different lengths, diameters, and styles of nozzle tips and needles are used on syringes. Syringes may also be available in a variety different volume sizes. Available volume sizes may range from about 0.3 mL to 60 mL, which is typically sufficient to cover the wide range of dosages required for most injections. Some syringes may also be equipped with safety features for reducing the incidence of accidental needle sticks.

There is often a problem with many conventional syringes in obtaining an accurate dosage measurement of small amounts of medicine. When low dosages of medication are prescribed, it can sometimes be difficult for the health care professional or the individual administering an injection to precisely measure the amount of fluid or gas to be injected. In some cases, for example, the gradations or markings of many low-dosage syringes such as 0.3 mL syringes are simply too close together for an accurate measurement to be made. On a 0.3 mL syringe, for example, there is often an insufficient amount of room for placement of the extremely small gradations. Some 0.3 mL syringes may have a maximum of 60 gradations on the syringe barrel, amounting to one gradation mark for each 0.005 mL (5 microliters). Some micro dosages are prescribed in increments lower than 0.0025 mL (2.5 microliters), however. Thus, the scale on those 0.3 mL syringes having 60 gradation marks still cannot measure many micro dosages of medication without interpolation.

Syringes are sometimes used in ocular procedures such as cataract extraction or intraocular lens (IOL) implantation for delivering a small amount of liquid (e.g. sodium hyaluronate) to the patient's eye during surgery. In some cases, injections are made to the human eye with dosage quantities of less than 0.005 mL (5 microliters), which is typically the smallest gradation available on a 0.3 mL syringe. As a result, accurate dosage is sometimes difficult and susceptible to error using 0.3 mL syringes, which often have measurement gradations that do not permit measurement in 0.005 mL or smaller increments.

Many medications given in low dosages can be considerably expensive. In the treatment of certain ocular diseases such as age related macular degeneration (ARMD), for example, a very small, less than 0.05 ml dosage of the pharmaceutical Lucentis® injected into the eyes of a patient may cost in excess of $1.000. Due to the high expense associated with such drugs, small dosage errors in the measurement of these drugs can result in significant expense.

Another growing area of low dosage injections is with small animals. The treatment of diabetes in cats, for example, frequently requires insulin injections of dosages less than 0.05 mL, and sometimes in increments as low as 0.005 mL. Dosages this minute are extremely difficult to read, even using a 0.3 mL syringe with 60 gradation lines. If a person caring for their pet at home misreads the gradations markings on the syringe, an inaccurate amount of medication may be injected into the animal.

One method used to minimize this measurement issue with pets is the increasing use of U-40 insulin, which is designed specifically for use with small animals such as dogs and cats. Traditionally, small diabetic pets were injected with U-100 insulin which is the same insulin used by humans. Now some veterinarians are prescribing U-40 insulin which is diluted to 40% the strength of U-100 insulin. By being diluted, more of the syringe can be filled with U-40 insulin, thus making it easier for the pet owner to accurately dose extremely small amounts of insulin. Because U-40 insulin costs significantly more than U-100 insulin, however, many small pet owners continue to use the more concentrated and difficult to administer U-100 insulin.

Often, the dilution of certain types of medicines is not a practical solution to reducing dosage errors. For some medications, for example, the medicine may not be compatible with dilution. Individuals administering such medications will continue to have to deal with the risk of measurement errors until a better solution is discovered.

Accordingly, there is a continuing need for new and alternative syringes that can be used to accurately deliver small dosages of fluids.

BRIEF SUMMARY

The present invention pertains to low-dosage syringes for use in accurately delivering small dosages of fluids. A low-dosage syringe in accordance with an illustrative embodiment can include an elongate syringe barrel having an interior chamber adapted to receive a supply of fluid, a plunger member slidably disposed within the interior chamber, and a tip member defining an inner lumen in fluid communication with the interior chamber. To permit small dosages of medicine to be administered, the syringe barrel may include a relatively thick sidewall, which in combination with the outer diameter and barrel length, may define a relatively small chamber for receiving small dosages of medicine. In some embodiments, for example, the interior chamber of the syringe barrel can be configured to receive 0.2 mL of fluid or less.

The outer diameter of the syringe barrel may be relatively large in comparison to the inner diameter to permit the user to easily grasp the syringe while also creating a relatively small interior chamber to receive medicine. In certain embodiments, the syringe barrel may further include a number of dosage markings disposed along the length of the syringe barrel, which can be configured to permit the user to quickly and accurately determine the amount of fluid contained within the chamber. In those embodiments in which the syringe has a 0.1 mL volume interior chamber, for example, the dosage markings may be disposed at 0.0025 mL or smaller increments along the length of the syringe barrel, allowing user to visually discern between subtle variations in fluid level within the chamber.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized. As used herein, the term "low-dosage" is intended to designate dosages less than 0.30 mL.

Figure 1:
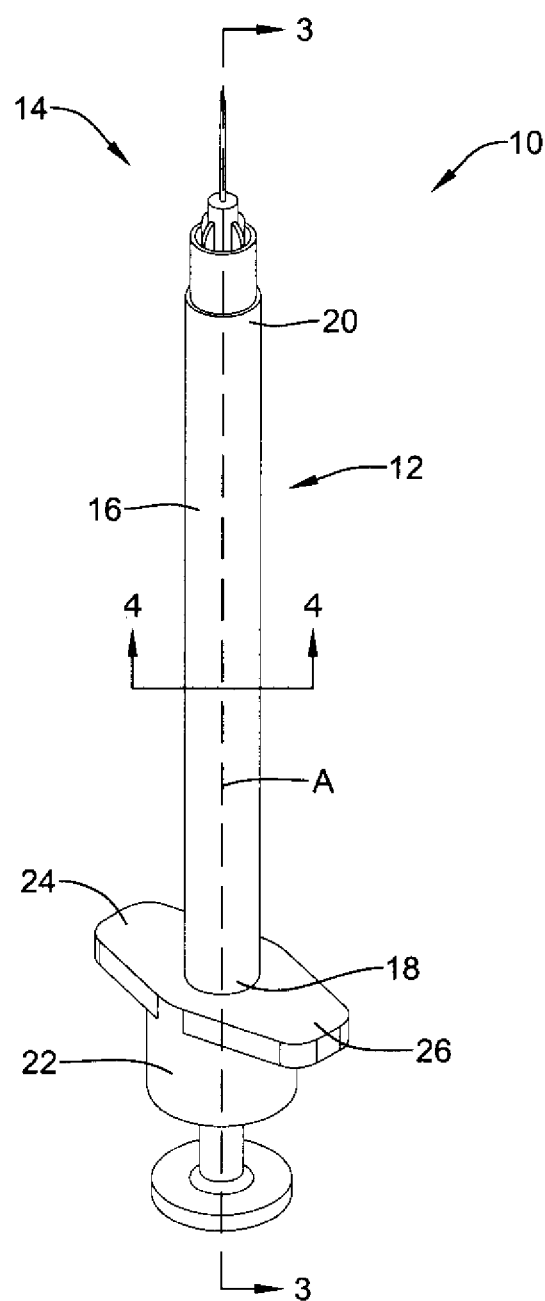
FIG. 1 is a perspective view of a low-dosage syringe in accordance with an illustrative embodiment.

Referring now to FIG. 1, a perspective view of an illustrative low-dosage syringe 10 will now be described. The syringe 10, illustratively a hypodermic syringe, includes a syringe barrel 12 equipped with a hollow hypodermic needle 14 that can be used for subcutaneously administering medications. The syringe barrel 12 can include a cylindrical syringe body 16 having a proximal end 18, a distal end 20, and a length extending along a longitudinal axis A of the syringe body 16 between the proximal and distal ends 18 and 20. The proximal end 18 of the syringe body 16 can be coupled to or formed integrally with a proximal base 22, and may include a set of thumb-grips 24,26 for gripping the syringe 10 with the user's fingers. The distal end 20 of the syringe body 16, in turn, can be coupled to or formed integrally with the hypodermic needle 14. Although a hypodermic needle 14 is shown in the illustrative embodiment, it should be understood that the syringe 10 can be equipped with a nozzle tip or other such tip member, as desired. In one alternative embodiment, for example, a screw-on nozzle tip can be threadably engaged onto the distal end 20 of the syringe body 16. In another alternative embodiment, a Luer-lock fitting may be used to secure the tip member onto the distal end 20 of the syringe body 16. In another alternative embodiment, a slip-tip fitting may be used to secure the tip member onto the distal end 20 of the syringe body 16.

Figure 2:
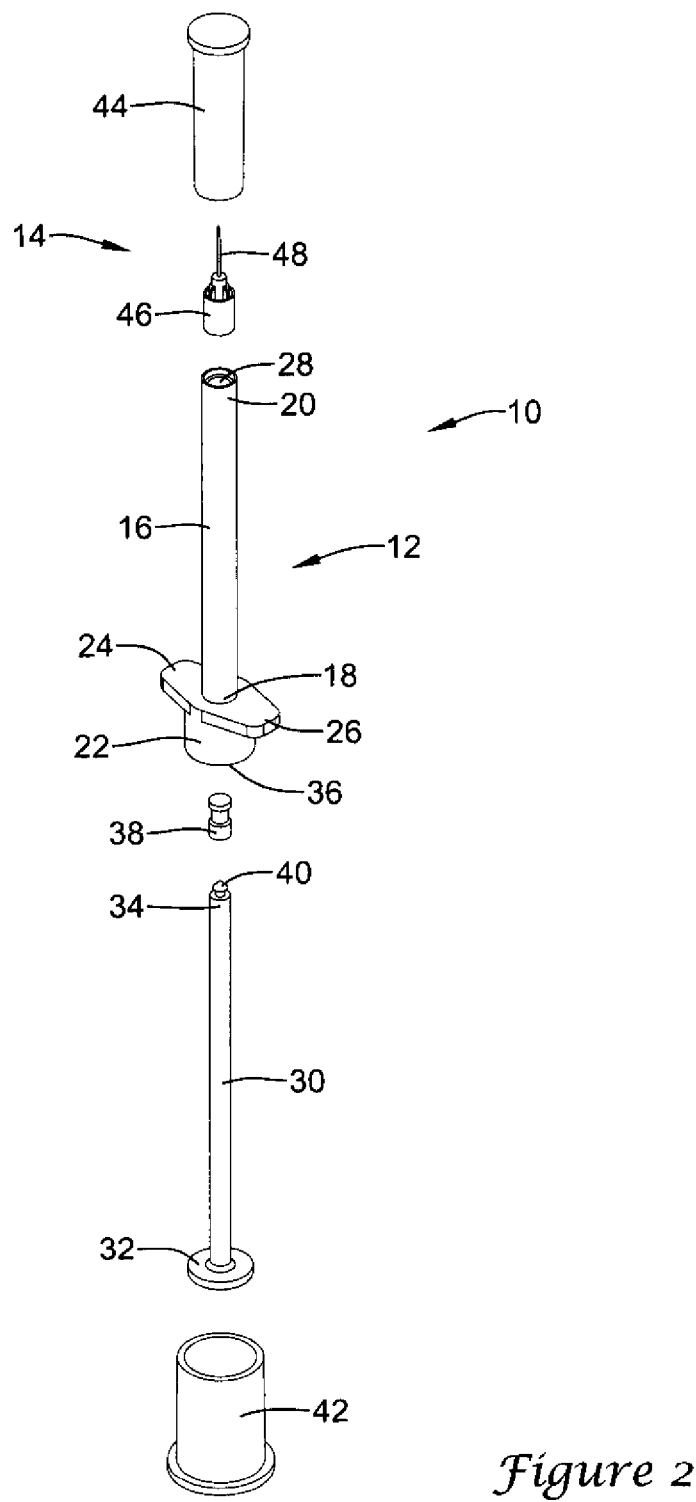
FIG. 2 is an assembly view showing several illustrative components of the low-dosage syringe of FIG. 1.

FIG. 2 is an assembly view showing several illustrative components of the low-dosage syringe 10 of FIG. 1. As can be further seen in FIG. 1, the syringe body 16 may define an interior chamber 28 adapted to receive a volume of liquid that can be aspirated and/or discharged through the needle 14 by actuation of a plunger member 30. The plunger member 30 may comprise an elongated rod have a proximal end 32 and a distal end 34, and can be configured to fit within a proximal port 36 of the base 22, allowing the user to advance and/or retract the plunger member 30 within the interior chamber 28 of the syringe body 16. Proximal movement of the plunger member 30, for example, may cause the syringe 10 to aspirate fluid into the interior chamber 28 of the syringe 10. Distal movement of the plunger member 30, in turn, may cause the syringe 10 to eject fluid from the interior chamber 28.

The distal end 34 of the plunger member 30 can be configured to drive an elastomeric piston 38, which forms a fluid-tight seal to prevent liquid contained within the interior chamber 28 from leaking out through the syringe body 16. The piston 38 may be formed from a natural or synthetic rubber, flexible polymer, or other suitable elastomeric material, and may have an outer dimension that is equal to or slightly larger than the inner diameter of the interior chamber 28. The piston 38 can be formed integrally with the plunger member 30 or can be coupled to the plunger member 30 via a connection nub 40, as shown.

The syringe 10 may be further equipped with a number of protective caps 42,44 that can be used to cover the plunger member 30 and hypodermic needle 14 prior to use. A first cap 42, for example, can be configured to fit over the proximal base 22 in order to prevent the inadvertent engagement of the plunger member 30. A second cap 44, in turn, can be configured to fit over the hypodermic needle 14 to prevent the user from accidentally contacting the tip 48, and to maintain the sterility of the needle 14. In use, the caps 42 and 44 can be removed from the proximal base 22 and the needle 14, allowing the user to then actuate the plunger member 30 proximally to aspirate fluid through the hollow needle tip 48. Although removable caps 42 and 44 are shown in the illustrative embodiment, it should be understood that other safety mechanisms can be incorporated into the syringe 10.

Figure 3:
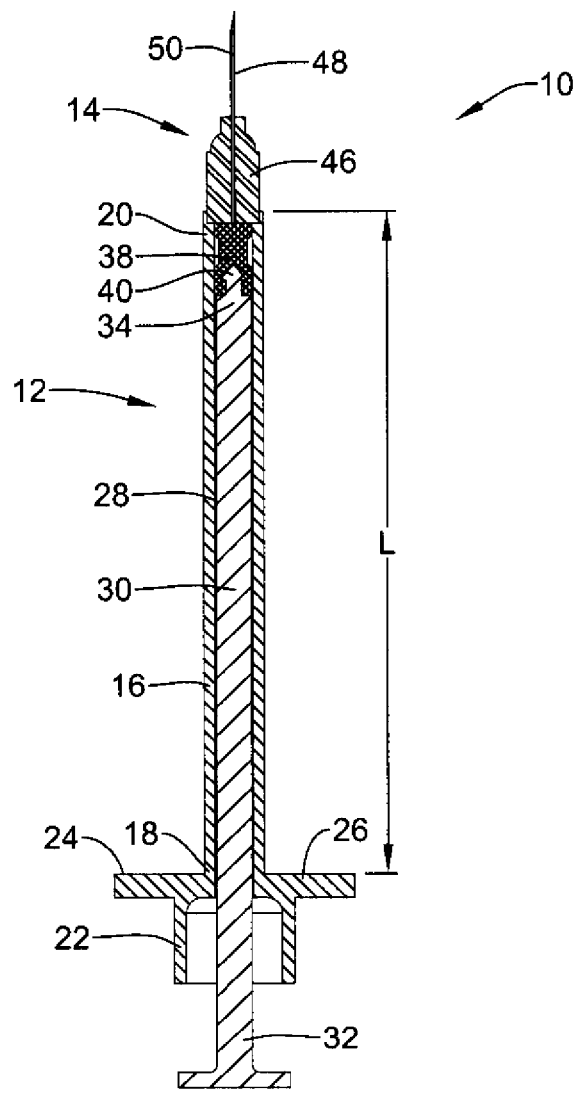
FIG. 3 is a side cross-sectional view of the illustrative low-dosage syringe along line 3-3 in FIG. 1.

FIG. 3 is a side cross-sectional view of the low-dosage syringe 10 along line 3-3 in FIG. 1. As can be further seen in FIG. 3 with the plunger member 30 fully advanced into the interior chamber 28, the elastomeric piston 38 can be configured to engage the base 46 of the hypodermic needle 14 with little or no dead space between the base 46 and the piston 38. In this position, the piston 38 blocks the fluid passage 50 within the needle tip 48, preventing the aspiration of fluid through the tip 48 and into the interior chamber 28. To draw fluid into the interior chamber 28, the user may pull the proximal end 32 of the plunger member 30 proximally while holding the syringe body 16 stationary with the thumb grips 24 and 26, causing fluid to enter the interior chamber 28 via the fluid passage 50. Once fluid has been drawn into the interior chamber 28, the user may then insert the needle tip 48 into a target site such as underneath the skin or in a fluid port, and then push the plunger member 30 distally until the piston 38 engages the base 46 of the needle 14.

The fluid capacity of the syringe 10 may be dependent on a number of factors, including the throw-length of the plunger member 30 and the inner diameter of the syringe body 16. The throw-length of the plunger member 30 may be determined in part based on the length L of the syringe body 16, which may vary depending on the overall fluid capacity of the syringe 10. In certain embodiments, for example, the syringe body 16 may have a length L of about 4 cm to 7 cm, and more specifically about 5 cm to 6 cm. The length L of the syringe body 16 may vary from these ranges, however.

Figure 4:
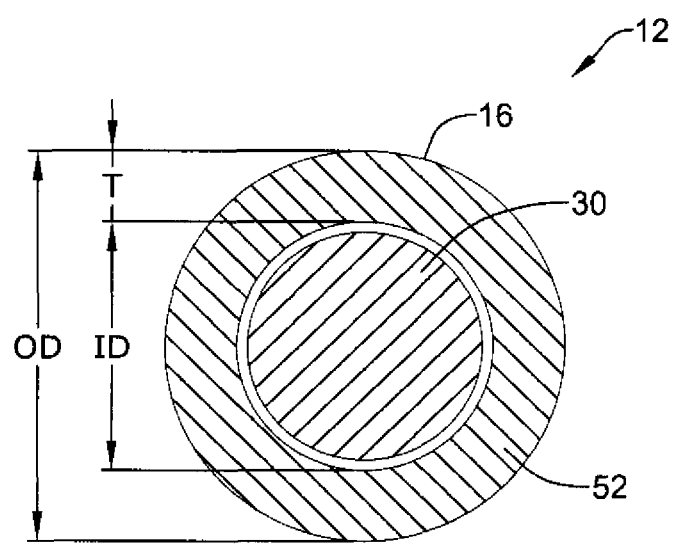
FIG. 4 is a transverse cross-sectional view of the syringe body along line 4-4 in FIG. 1.

FIG. 4 is a transverse cross-sectional view of the syringe body 16 alone line 4-4 in FIG. 1. As shown further in FIG. 4, the syringe body 16 may include a sidewall 52 defining an outer diameter OD, an inner diameter ID, and a wall thickness T. The outer diameter OD may be relatively large in comparison to the inner diameter ID, which as discussed in greater detail below, allows the user to better view the gradation markings on the syringe body 16, and enables the user to better manipulate the syringe 10 with their fingers. In certain embodiments, for example, the sidewall 52 may have an outer diameter OD of about 3.5 mm to about 6.5 mm, and more specifically about 4.75 mm to about 6 mm whereas the inner diameter ID may be about 0.25 mm to about 3 mm, and more specifically about 1.5 mm to about 2 mm. The inner and outer diameters may vary from these ranges, however.

The ratio of the wall thickness T to the outer diameter OD can be made large, forming a relatively small interior chamber 28 for holding low dosages of medicine within the syringe 10. In some embodiments, for example, the ratio of the wall thickness T to the outer diameter OD can be in the range of about 0.05 to 0.5, and more specifically between 0.275 and 0.425. For a wall thickness T of about 1.6 mm and an outer diameter OD of about 5 mm, for example, the ratio of the wall thickness T to the outer diameter OD of the syringe 10 is about 0.32. Other ratios greater or smaller than this are also possible, however.

By increasing the wall thickness T of the sidewall 52 in lieu of adjusting the amount of dilution of the medicine as is normally done with smaller dosage syringes, the outer diameter OD of the syringe 10 may remain relatively large, similar to syringes having fluid capacities in excess of 0.3 mL. In addition, by maintaining a relatively large outer diameter OD while reducing the volume capacity of the syringe 10 using a relatively large wall thickness T, the user is better able to view the gradation markings on the sidewall 52 and is better able to grip the syringe body 16 with their fingers. The use of a relatively large wall thickness T may also facilitate the manufacturability of the syringe 10 in some cases.

The ratio of the wall thickness T to the length L of the syringe body 16 can also be made relatively large in order to form a smaller interior chamber 28 for holding low dosages of medicine within the syringe 10. In some embodiments, for example, the ratio of the wall thickness T to the length L can be made in the range of about 0.005 to 0.05, and more specifically about 0.02 to 0.04. For a wall thickness T of about 1.6 mm and a length of about 55 mm, for example, the ratio of the wall thickness T to the length L is about 0.29. Other ratios greater or smaller than this are possible, however.

The relative dimensions of the syringe body 16, including the ratio of the wall thickness T to the outer diameter OD and the ratio of the wall thickness T to the length L, may be selected so as to create an interior chamber 28 having a volume capacity of less than 0.3 mL of fluid. In one illustrative embodiment, for example, the outer diameter OD, wall thickness T, and length L of the syringe body 16 may be selected so as to form a syringe having a fluid capacity of about 0.1 mL.

Figure 5:
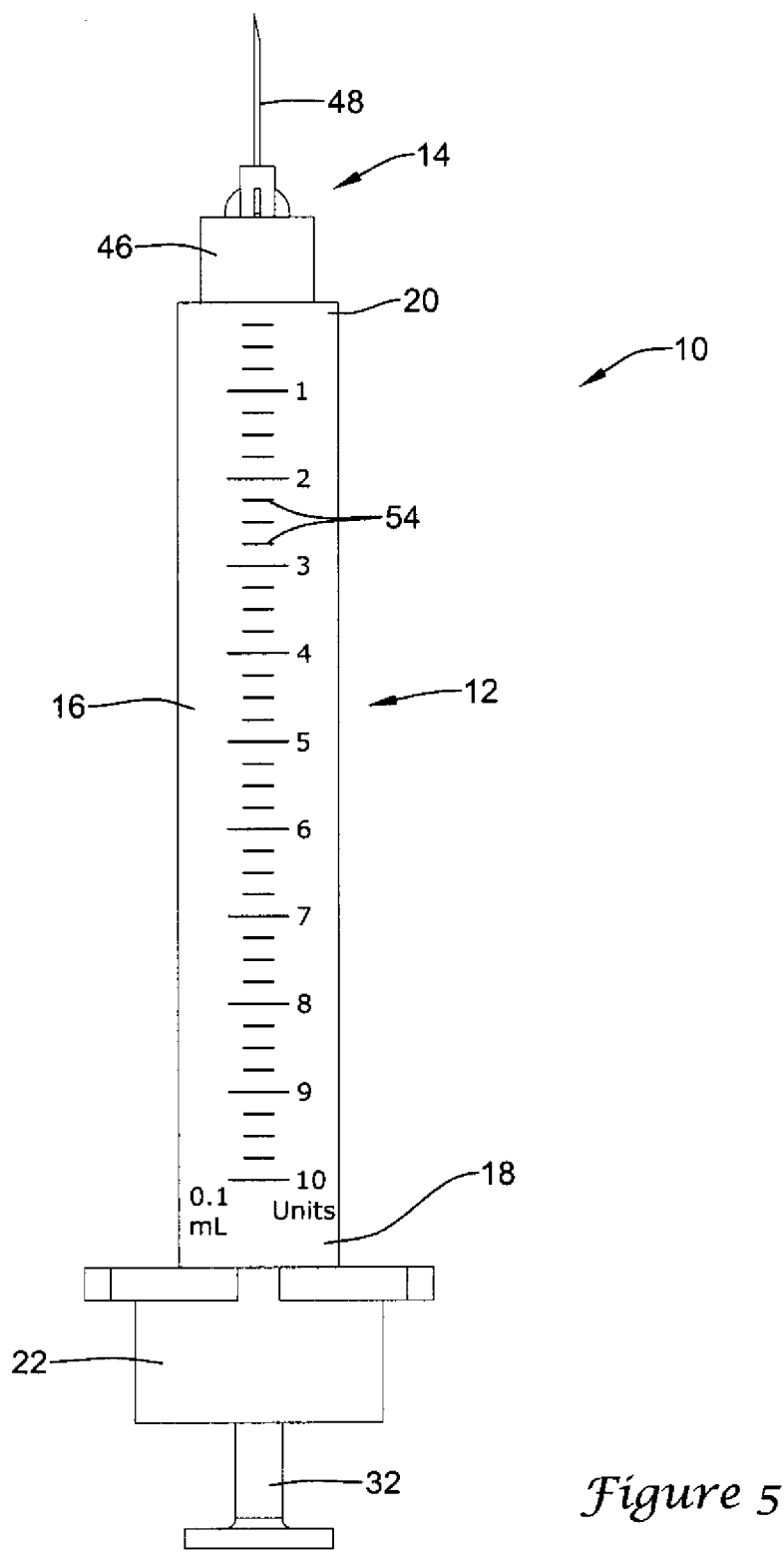
FIG. 5 is a perspective view showing several illustrative markings on the low-dosage syringe of FIG. 1.

FIG. 5 is a perspective view showing a 0.1 mL volume syringe in accordance with an illustrative embodiment having a number of gradation markings 54 located along the length of the syringe body 16. In the illustrative embodiment depicted, the gradation markings 54 are each spaced apart at 0.0025 ml increments along the length of the syringe body 16, which due to the relatively large outer diameter OD, can be easily viewed by the user. For diabetic users, the gradation markings 54 may also be labeled in terms of insulin units, as further shown in FIG. 5. The number and labeling of the gradation markings 54 can be altered, however, depending on the fluid capacity of the syringe and its intended use.

In use, the ability to quickly and easily view the volume of fluid within the syringe 10 helps the user to more accurately meter fluid into the syringe 10.

Having thus described the several embodiments of the present invention, those of skill in the art will readily appreciate that other embodiments may be made and used which fall within the scope of the claims attached hereto. It will be understood that this disclosure is, in many respects, only illustrative. Changes can be made with respect to various elements described herein without exceeding the scope of the invention.

What is claimed is:

1. A low-dosage syringe, comprising:
    an elongate syringe barrel having a proximal end, a distal end, a length, and a sidewall defining an interior chamber adapted to receive a supply of fluid, said interior chamber having a single inner diameter, an outer diameter, and a wall thickness;
    a plunger member slidably disposed within the interior chamber, said plunger being of substantially uniform cross-section and having an elastomeric distal piston;
    a tip member disposed within the distal end of the syringe barrel, the tip member defining an inner lumen in fluid communication with the interior chamber; and
    wherein the ratio of the wall thickness to the outer diameter is in the range of about 0.05 to 0.5,
    further wherein the interior chamber has a volume equal to or less than 0.25 mL.

2. The low-dosage syringe of claim 1, wherein the interior chamber has a volume equal to or less than 0.2 mL.

3. The low-dosage syringe of claim 1, wherein the interior chamber has a volume equal to or less than 0.15 mL.

4. The low-dosage syringe of claim 1, wherein the interior chamber has a volume equal to or less than 0.1 mL.

5. The low-dosage syringe of claim 1, wherein the interior chamber has a volume equal to or less than 0.05 mL.

6. The low-dosage syringe of claim 1, wherein the interior chamber has a volume in the range of about 0.05 mL to 0.3 mL.

7. The low-dosage syringe of claim 1, wherein the ratio of the wall thickness to the outer diameter of the sidewall is equal to or greater than 0.25.

8. The low-dosage syringe of claim 1, wherein the ratio of the wall thickness to the outer diameter is equal to or greater than 0.275.

9. The low-dosage syringe of claim 1, wherein the ratio of the wall thickness to the outer diameter is equal to or greater than 0.30.

10. The low-dosage syringe of claim 1, wherein the ratio of the wall thickness to the outer diameter is equal to or greater than 0.35.

11. The low-dosage syringe of claim 1, wherein the ratio of the wall thickness to the outer diameter is equal to or greater than 0.40.

12. The low-dosage syringe of claim 1, wherein the ratio of the wall thickness to the outer diameter is equal to or greater than 0.45.

13. The low-dosage syringe of claim 1, wherein the ratio of the wall thickness to the length of the syringe barrel is equal to or greater than 0.005.

14. The low-dosage syringe of claim 13, wherein the length of the syringe barrel is in the range of about 3 cm to 7 cm.

15. The low-dosage syringe of claim 13, wherein the length of the syringe barrel is about 5.5 cm.

16. The low-dosage syringe of claim 1, wherein the syringe further includes a means for visually measuring the amount of fluid contained within the interior chamber.

17. The low-dosage syringe of claim 16, wherein said means for visually measuring the amount of fluid contained within the interior chamber includes a plurality of dosage markings disposed at 0.0025 mL or less increments along the length of the syringe barrel.

18. The low-dosage syringe of claim 1, wherein the plunger member includes an elongate rod coupled to an elastomeric piston, wherein the elastomeric piston forms a substantially fluid tight seal with the wall of the interior chamber.

19. The low-dosage syringe of claim 1, wherein the tip member includes a needle tip.

20. The low-dosage syringe of claim 1, wherein the tip member includes a nozzle tip.

21. The low-dosage syringe of claim 1, wherein the tip member is releasably secured to the distal end of the syringe barrel.

22. The low-dosage syringe of claim 1, wherein the tip member is releasably secured to the distal end of the syringe barrel using a Luer-lock fitting.

23. The low dosage syringe of claim 1, wherein the tip member is releasably secured to the distal end of the syringe barrel using a slip-tip fitting.

24. The low-dosage syringe of claim 1, wherein the tip member is formed integrally with the distal end of the syringe barrel.

25. The low-dosage syringe of claim 1, wherein the syringe is a safety syringe.

26. The low-dosage syringe of claim 1, wherein the elastomeric distal piston is configured to engage the tip member without significant dead space between the tip member and the elastomeric piston when the plunger member is fully advanced into the interior chamber.

27. A low-dosage syringe, comprising:
an elongate syringe barrel having a proximal end, a distal end, a length, and a sidewall defining an interior chamber adapted to receive a supply of fluid, said interior chamber having a single inner diameter, an outer diameter, and a wall thickness;
a plunger member slidably disposed within the interior chamber, said plunger being of substantially uniform cross-section and having an elastomeric distal piston;
a tip member disposed within the distal end of the syringe barrel, the tip member defining an inner lumen in fluid communication with the interior chamber;
wherein the interior chamber has a volume less than about 0.3 mL; and
wherein the ratio of the wall thickness to the outer diameter of the sidewall is in the range of about 0.05 to 0.5.

28. A low-dosage syringe, comprising:
an elongate syringe barrel having a proximal end, a distal end, a length, and a sidewall defining an interior chamber adapted to receive a supply of fluid, said interior chamber having a single inner diameter, an outer diameter, and a wall thickness;
a plunger member slidably disposed within the interior chamber, said plunger being of substantially uniform cross-section and having an elastomeric distal piston;
a tip member disposed within the distal end of the syringe barrel, the tip member defining an inner lumen in fluid communication with the interior chamber;
wherein the syringe barrel chamber has a volume less than about 0.3 mL;
wherein the ratio of the wall thickness to the outer diameter of the sidewall is in the range of about 0.05 to 0.5;
wherein the outer diameter of the sidewall is not less than about 5 mm; and
wherein the elastomeric distal piston is configured to engage the tip member without significant dead space between the tip member and the elastomeric piston when the plunger member is fully advanced into the interior chamber.

* * * * *